US012577532B2

(12) United States Patent
Sugaya et al.

(10) Patent No.: US 12,577,532 B2
(45) Date of Patent: Mar. 17, 2026

(54) XENO-FREE AND TRANSGENE-FREE REPROGRAMING OF MESENCHYMAL STEM CELLS TOWARD NEURAL PROGENITOR CELLS

(71) Applicants: UNIVERSITY OF CENTRAL FLORIDA RESEARCH FOUNDATION, INC., Orlando, FL (US); INSTITUTE FOR SCIENTIFIC RESEARCH AND TECHNOLOGY SERVICES (INDICASAT), City of Knowledge (PA)

(72) Inventors: Kiminobu Sugaya, Orlando, FL (US); Luis Sebastian Alexis Valerio, La Chorrera (PA)

(73) Assignees: UNIVERSITY OF CENTRAL FLORIDA RESEARCH FOUNDATION, INC., Orlando, FL (US); INSTITUTE FOR SCIENTIFIC RESEARCH AND TECHNOLOGY SERVICES (INDICASAT), City of Knowledge (PA)

( * ) Notice: Subject to any disclaimer, the term of this patent is extended or adjusted under 35 U.S.C. 154(b) by 1088 days.

(21) Appl. No.: 17/613,993

(22) PCT Filed: May 26, 2020

(86) PCT No.: PCT/US2020/034553

§ 371 (c)(1),
(2) Date: Nov. 24, 2021

(87) PCT Pub. No.: WO2020/243091

PCT Pub. Date: Dec. 3, 2020

(65) Prior Publication Data

US 2022/0348867 A1 Nov. 3, 2022

Related U.S. Application Data

(60) Provisional application No. 62/852,388, filed on May 24, 2019.

(51) Int. Cl.
*C12N 5/0797* (2010.01)
*A61K 35/30* (2015.01)

(52) U.S. Cl.
CPC ............ *C12N 5/0623* (2013.01); *A61K 35/30* (2013.01); *C12N 2500/38* (2013.01); *C12N 2500/40* (2013.01); *C12N 2501/06* (2013.01); *C12N 2501/11* (2013.01); *C12N 2501/113* (2013.01); *C12N 2501/91* (2013.01); *C12N 2502/088* (2013.01); *C12N 2506/1346* (2013.01)

(58) Field of Classification Search
CPC .............. C12N 5/0623; C12N 2500/38; C12N 2500/40; C12N 2501/06; C12N 2501/11; C12N 2501/113; C12N 2501/91; C12N 2502/088; C12N 2506/1346; A61K 35/30
USPC ........................................................ 424/93.7
See application file for complete search history.

(56) References Cited

U.S. PATENT DOCUMENTS

| | | | | |
|---|---|---|---|---|
| 2009/0304647 | A1* | 12/2009 | Qu | A61P 25/28 435/372 |
| 2016/0130554 | A1 | 5/2016 | Almeida-Porada et al. | |
| 2017/0267971 | A1* | 9/2017 | Han | C12N 5/0622 |
| 2019/0119666 | A1 | 4/2019 | Kim | |

FOREIGN PATENT DOCUMENTS

| | | | |
|---|---|---|---|
| WO | 2017155166 | A1 | 9/2017 |
| WO | WO2017155166 | * | 9/2017 |
| WO | 2020243091 | A1 | 12/2020 |

OTHER PUBLICATIONS

Takeda et al., Neuronal Differentiation of Human Mesenchymal Stem Cells Using Exosomes Derived from Differentiating Neuronal Cells, PLoS ONE, 10(8), (2015), pp. 1-15.*
Diomede et al., 5-Aza Exposure Improves Reprogramming Process Through Embryoid Body Formation in Human Gingival Stem Cells, Frontiers in Genetics, vol. 9, Article 419, (2018), pp. 1-11.*
Christman, 5-Azacytidine and 5-aza-2'-deoxycytidine as inhibitors of DNA methylation: mechanistic studies and their implications for cancer therapy, Oncogene, vol. 21, (2002), pp. 5483-5495.*
PCT/US2020/034553, PCT Search Report & Written Opinion, mailed Oct. 15, 2020, 12 pages.
Kassis, I. et al., "Isolation of mesenchymal stem cells from G-CSF-mobilized human peripheral blood using fibrin microbeads".
Kern, Susanne et al., "Comparative Analysis of Mesenchymal Stem Cells from Bone Marrow, Umbilical Cord Blood, or Adipose Tissue", Stem Cells, 2006, vol. 24, pp. 1294-1301.
Valerio, Luis Sebastian Alexis et al., "Xeno- and transgene-free reprogramming of mesenchymal stem cells toward the cells expressing neural markers using exosome treatments", Plos One, Oct. 13, 2020, 14 pages.
Zhang, Yi et al., "Comparison of mesenchymal stem cells from human placenta and bone marrow", Chinese Medical Journal, 2004, vol. 117, issue 6, pp. 882-887.

* cited by examiner

*Primary Examiner* — Jennifer M. H. Tichy
(74) *Attorney, Agent, or Firm* — Timothy H. Van Dyke; Wolter Van Dyke Davis, PLLC

(57) ABSTRACT

Disclosed herein are methods and materials for transdifferentiating mesenchymal stem cells into neural progenitor cells.

6 Claims, 6 Drawing Sheets

XENO-FREE AND TRANSGENE-FREE REPROGRAMING OF MESENCHYMAL STEM CELLS TOWARD NEURAL PROGENITOR CELLS

BACKGROUND

The process of reprogramming specialized cells to become a desired type of cells for uses on clinics or basic sciences, represents invaluable tool for regenerative medicine. In order to tackle neurological diseases, it is of interest the development of neural progenitors, which originates from Neural Stem Cells (NSC), which resides on the hippocampus of the brain. However, it is highly risky, invasive and costly to obtain a biopsy from brain-patients for isolation of NSC for culture. Mesenchymal Stem Cells (MSC) may become the feasible option because they reside in many tissues from which is easy to take samples (i.e., adipose tissue or blood), they are abundant in the body, posses multi-potency, self renewal activity and stem cell plasticity. However, its use for neurological diseases is challenging since they do not originate neural cells, which originally results from ectodermal-germ layer commitment. If it can be shown that MSC can be induced to neural progenitors using xeno and gene free strategies, then this technology could have the potential to be used at clinics in a safe manner.

DETAILED DESCRIPTION

Figure 1:
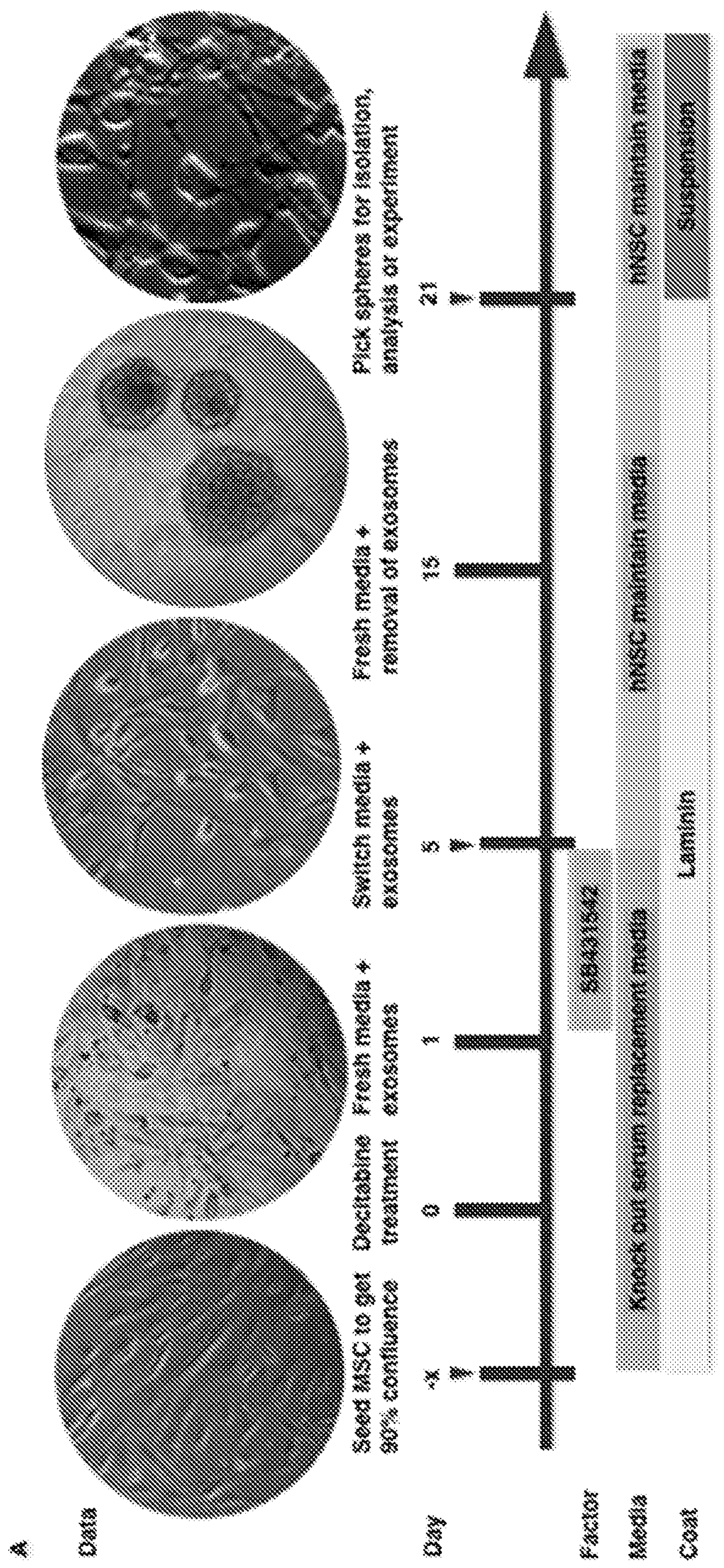
FIG. 1 provides a schematic of a method for reprograming mesenchymal stem cells into neural progenitor cells.

Herein it is demonstrated that MSC treated with 5-aza-2'-deoxycytidine (decitabine) develop capability to transdifferentiate into neural progenitors when provided exosomes derived from Neural Stem Cells (NSC) as a source of linage specific signals in three weeks. The results provided herein demonstrate that reprogramming of cells from mesoderm germ layer show successful transdifferentiation towards ectodermal cells bypassing intermediate pluripotent stage in xeno and transgenes free conditions. This cost effective and time efficient method to develop neural progenitors will accelerate development of neuroregenerative therapies.

The embodiments disclosed herein have the benefit over currently available technology by using an epigenetic modifier and exosomes from human neural stem cells as a lineage cell specific commitment. In a specific embodiment, the epigenetic modifier comprises 5'-aza-2'-deoxycitidine or 5-Azacytidine, or a combination thereof.

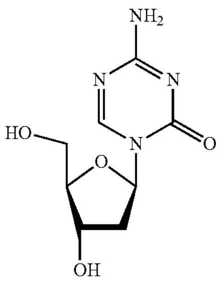 [SMILES: Nc1ncn([C@H]2C[C@@H](O)[C@@H](CO)O2)c(=O)n1]

5′-aza-2′-deocycitidine

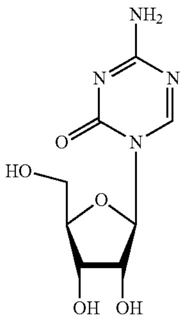

5-Azacytidine

The resultant cells are capable of expansion and differentiating towards neural cells, without the need to transform the cells with transgenes. In addition, embodiments described herein are time efficient and cost effective, as they can be used to develop neural progenitors in less than three weeks. In one embodiment, provided is a method that involves treating cells with small molecule drug that modulates epigenetics rather than use transgenes. Also, disclosed is a use of culture media and a scaffold free of animal products, which represents an advantage for uses on clinics.

The embodiments disclosed herein may be used for studies of neurodegenerative diseases by developing patient-specific neural progenitors. For example, a mesenchymal stem cell sample can be obtained from a subject such as from blood or marrow, and the cells subjected to treatment with 5-asa-2'-deoxycytidine and exosomes from a neural stem cell population. The resultant cells can be used for screening assays and tests to screen for and develop novel bioactive molecules. This technology also has the potential to be used at medical clinics because the method embodiments do not need to use completely free of transgenes and animal products, which made neural progenitors compatible, especially, if the reprogrammed cells are for autologous therapies. The neural stem cells produced by the methods described herein may be administered autologously to the patient from which they were obtained or administered as an allogenic cell population to a recipient.

Definitions

The terms "animal," "patient," or "subject," as used herein, mean any animal (e.g., mammals, (including, but not limited to humans, primates, dogs, cattle, cows, horses, kangaroos, pigs, sheep, goats, cats, rabbits, rodents, and transgenic non-human animals), and the like, which are to be the recipient of a particular treatment.

Typically, the terms "animal" "subject" and "patient" are used interchangeably herein in reference to a human subject or a rodent. The preferred animal, patient, or subject is a human.

The term "administer" and grammatical forms thereof as it applies to a human, mammal, mammalian subject, animal, veterinary subject, placebo subject, research subject, experimental subject, cell, tissue, organ, or biological fluid, refers without limitation to contact of cells or composition to the subject, cell, tissue, organ, or biological fluid, and the like. The cells or composition may be administered by direct transplantation such as implantation into the central or peripheral nervous system. For example, cells can be implanted directly into a region of the brain. Cells or composition may optionally be administered subcutaneously, intravenously, intraarterially, intratumorally, parenterally, intraperitoneally, intramuscularly, intraocularly, intraosseally, epidurally, intradurally, and the like.

The terms "treat", "treating" or "treatment of" as used herein refers to providing any type of medical management to a subject. Treating includes, but is not limited to, administering a composition to a subject using any known method. for purposes such as curing, reversing, alleviating, reducing the severity of, inhibiting the progression of, or reducing the likelihood of a disease, disorder, or condition or one or more symptoms or manifestations of a disease, disorder or condition.

The term "epigenetic modifier" as used herein refers to an agent that modifies epigenetic status of a DNA. Examples of an epigenetic modifier include but are not limited to 5-aza-2'-deoxycytidine (CAS Number 2353-35-5, also known as decitabine) or 5-Azacytidine (CAS Number 320-67-2).

The term "reprogram (ing)" as used herein refers to transdifferentiation from one cell lineage to another cell lineage. For example, reprogramming includes converting MSCs to neural progenitor cells. Reprogramming MSCs into neural progenitor cells may bypass a pluripotent state.

The term "epigenetic status" as used herein refers to status of DNA accessibility as a function of DNA methylation and chromatin structure (e.g. histone methylation). Increased epigenetic status with respect to DNA and chromosomes, or regions thereof, means that the DNA and chromosomes, or regions thereof, are more accessible. Higher epigenetic status of DNA, chromosomes or regions thereof, provides a higher probability of expression of genes including genes responsible for reprogramming.

As used herein, by the term "effective amount," "amount effective," "therapeutically effective amount," or the like, it is meant an amount effective at dosages and for periods of time necessary to achieve the desired result. These terms refers to an amount of an enumerated agent, which, when administered or co-administered in a proper dosing regimen, is sufficient to reduce or ameliorate the severity, duration, or progression of the disorder being treated (e.g., neurological deficit) to prevent the advancement of the disorder being treated, cause the regression of the disorder being treated), or enhance or improve the prophylactic or therapeutic effects(s) of another therapy. The full therapeutic effect does not necessarily occur by administration of one dose and may occur only after administration of a series of doses. Thus, a therapeutically effective amount may be administered in one or more administrations per day for successive days.

For the purposes of promoting an understanding of the principles and operation of the disclosure and embodiments, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to those skilled in the art to which the invention pertains.

As used herein, the singular forms "a," "an," and "the" are intended to include the plural forms as well, unless the context clearly indicates otherwise these terms do not denote a limitation of quantity, but rather denote the presence of at least one of the referenced item.

The terms "about" or "approximately" as used herein when referring to a measurable value such as a parameter, an amount, concentration, a temporal duration, and the like, are meant to encompass variations of and from the specified value, such as variations of +/−10% or less, +1-5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

Furthermore, to the extent that the terms "including," "includes," "having," "has," "with," or variants thereof are used in either the detailed description and/or the claims, such terms are intended to be inclusive in a manner similar to the term "comprising." Moreover, unless specifically stated, any use of the terms first, second, etc., does not denote any order, quantity or importance, but rather the terms first, second, etc., are used to distinguish one element from another. The modifier "about" used in connection with a quantity is inclusive of the stated value and has the meaning dictated by the context. It is to be noted that all ranges disclosed within this specification are inclusive and are independently combinable.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. As a non-limiting example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 7. As another non-limiting example, a range of "between 20 and 10" can also include the values 20, 10.

Extracellular Vesicles

As used herein, the term "extracellular vesicle (EV)" Extracellular vesicles (EV) encompass a number of different membraned vesicles produced by cells, the names of which include, for example, microvesicles, epididimosomes, argosomes, exosome-like vesicles, microparticles, promininosomes, prostasomes, dexosomes, texosomes, archeosomes, oncosomes, and exersornesectosomes, microparticles and shedding microvesicles. Extracellular vesicles (EV) circulate through body fluids, including blood, plasma, serum and urine. Circulating EV may contain exosomes and microvesicles (MV).

As used herein, the term "extracellular vesicles" refers to a membrane (e.g., lipid bilayer)-containing vesicle released (secreted) by or formed by direct budding off of cells to the extracellular environment by different cell types. Extracellular vesicles encompasses "exosomes," "microvesicles (MVs)," and "apoptotic bodies, Extracellular vesicles are present in many, if not all, eukaryotic fluids, including blood, urine and cultured medium of cell cultures. Extracellular vesicles, in particular exosomes or MVs, are known for their role in cell to cell communications and have demonstrated an ability to unload their contents and contribute to the transformation of normal and stem cells to cancerous states.

As part of the formation and release of extracellular vesicles, unwanted molecules are eliminated from cells. However, cytosolic and plasma membrane proteins are also incorporated during these processes into the extracellular vesicles, resulting in extracellular vesicles having particle size properties, lipid bilayer functional properties, and other unique functional properties that allow the vesicles to potentially function to carry their payload.

An "exosome" refers to a small membrane extracellular vesicle of −30-300 nm or −40-120 nm diameter that is secreted from producing cells into the extracellular environment, as described initially by Trams, E. G. et al., 1981, Biochim. Biophys. Acta, 645(I):63-70. The surface (membrane surface) of an exosome comprises a lipid bilayer from the membrane of the donor cell, and the lumen of the exosome is topologically the same as the cytosol from the cell that produces the exosome. The exosome contains proteins, RNAs, lipids, and carbohydrates of the producing cell, though some may be modified or added to the exosome after its release from the cell, either through natural processes or by experimental manipulation. For example, exosomes are commonly formed by their secretion from the endosomal membrane compartments of cells as a consequence of the fusion of multivesicular bodies with the plasma membrane. The multivesicular bodies (MVBs) are formed by inward budding from the endosomal membrane and subsequent pinching off of small vesicles into the luminal space. The internal vesicles present in the MVBs are then released into the extracellular fluid as so-called exosomes or extracellular vesicles.

The term "microvesicle" (abbreviated "MV") refers to a single membrane vesicle secreted by different cell types. MV may have a diameter (or largest dimension where the particle is not spheroid) of between about 10 nm to about 5000 nm (e.g., between about 50 nm and 1500 nm, between about 75 nm and 1500 nm, between about 75 nm and 1250 nm, between about 50 nm and 1250 nm, between about 30 nm and 1000 nm, between about 50 nm and 1000 nm, between about 100 nm and 1000 nm, between about 50 nm and 750 nm, etc.). Microvesicles originate from cells, yet different subpopulations of microvesicles may exhibit different surface/lipid characteristics. Typically, at least part of the membrane of the microvesicle is directly obtained from a cell (also known as a donor cell). Microvesicles may originate from cells by membrane inversion, exocytosis, shedding, blebbing, and/or budding. Depending on the manner of generation (e.g., membrane inversion, exocytosis, shedding, or budding), microvesicles may exhibit different surface/lipid characteristics. Illustrative microvesicle markers include integrins, selectins and CD40. Microvesicles have been called by alternative names in the art, such as, for example, EV, exosomes, membrane particles, exosome-like particles, and apoptotic vesicles.

Neural Stem Cells

The term "neural stem cell", as used in the present specification, describes a cell that is capable of undergoing greater than 30 cell divisions while maintaining the potency to generate both neurons and glia (e.g. neurons, astrocytes and oligodendrocytes). Preferably, said cells are capable of undergoing greater than 40, more preferably greater than 50, most preferably unlimited such cell divisions. Neural stem markers include MSI1, Sox1, Nestin, Pax6, and stemness markers Oct4 and nanog Neural stem cells are capable of dividing either symmetrically, or asymmetrically. When dividing symmetrically, the neural stem cell divides to form two daughter neural stem cells or two committed progenitors, though unless otherwise specified symmetrical division refers herein to symmetrical self renewal; when dividing asymmetrically, the neural stem cell divides to form one daughter neural stem cell, and one committed progenitor (e.g. either a neuron or a glial progenitor).

It is possible to derive neural stem cells from a wide variety of sources. For example, neural stem cells can be derived directly from embryos, from adult tissue, from fetal tissue, or from embryonic stem (ES) cells (either wild-type or genetically modified ES cells). Preferably, the neural stem cells are derived from mouse or human ES cells, or are derived from mouse or human fetal cells.

Neural stem cells can be derived from, inter alia, humans, primates, rodents, and birds. Preferably, the neural stem cells are derived from mammals, especially mice, rats and humans.

The term "neural progenitor cell(s)" refers to a cell that has the capacity to proliferate and differentiate into more than one cell type (e.g. neurons, astrocytes and oligodendrocytes). Neural progenitor cells can therefore be unipotent, bipotent or multipotent. A distinguishing feature of a neural progenitor cell is that, unlike a stem cell, it has a limited proliferative ability and does not exhibit self-renewal. In a more specific embodiment, neural progenitor cells are characterized by the expression of SRY (sex determining region Y)-box 1 (SOX1), CD90, GFAP, SRY (sex determining region Y)-box 2 (SOX2) and/or paired box 6 (PAX6).

Mesenchymal Stem Cells

As used herein the phrase "mesenchymal stem cells" (MSCs) refers to fetal or postnatal (e.g., adult) cells which differentiate (either terminally or non-terminally) to give rise to cells of a mesenchymal and under certain conditions mesodermal cell lineage and which are also capable of dividing to yield stem cells. The cells can be primary cells or derived from mesenchymal stem cell lines.

Thus, mesenchymal stem cells give rise to one or more mesenchymal tissues (e.g., adipose, osseous, cartilaginous, elastic and fibrous connective tissues, myoblasts) as well as to tissues other than those originating in the embryonic mesoderm (e.g., neural cells) depending upon various influences from bioactive factors such as cytokines. Cells differentiated into any of these lineages are envisaged by the present teachings to be useful and capable of transdifferentiation as well.

Mesenchymal stem cells are also referred to as marrow stromal cells or multipotent stromal cells.

MSCs according to the present teachings are adherent cells which express the surface markers CD105, CD90, CD44 and CD29 and which do not express the CD34, CD 31, CD144 and CD133 surface markers.

Mesenchymal stem cells as used herein can be obtained from a plurality of tissues including bone marrow, embryonic yolk sac, placenta, umbilical cord, fetal and adolescent skin, peripheral blood and other tissues. However, their abundance in the BM far exceeds their abundance in other tissues and as such isolation from BM is presently preferred.

A method of isolating mesenchymal stem cells from peripheral blood is described by Kassis et al [Bone Marrow Transplant. 2006 May; 37(10):967-76]. A method of isolating mesenchymal stem cells from placental tissue is described by Zhang et al [Chinese Medical Journal, 2004, 117 (6):882-887]. Methods of isolating and culturing adipose tissue, placental and cord blood mesenchymal stem cells are described by Kern et al [Stem Cells, 2006; 24:1294-1301].

According to an embodiment, the mesenchymal stem cells are isolated from humans.

MSCs are typically first plated on adherent (e.g., polystyrene plastic) surfaces (e.g. in a flask) and mesenchymal stem cells are isolated by removing non-adherent cells. Thereafter, mesenchymal stem cells are further purified using methods which are well known in the art such as antibody-based techniques, e.g., FACS or MAC using mesenchymal stem cell markers (positive and/or negative selection).

Therapeutic Methods

Disclosed herein are methods for using neural progenitor cells (NPCs) provided herein to treat an animal in need thereof by administering the NPCs thereto. In certain embodiments, the subject has a neurological deficit that can be treated by administration of said NPCs, such as a deficit caused by a neurodegenerative disease, a traumatic injury, a neurotoxic injury, ischemia, a developmental disorder, a disorder affecting vision, an injury or disease of the spinal cord, a demyelinating disease, an autoimmune disease, an infection, an inflammatory disease, or corporal disease, disorder, injury, trauma, malfunction, degeneration or loss. The NPCs are capable of migrating to an area of tissue damage, differentiating in a tissue-specific manner and functioning in a manner that reduces the neurological or corporal deficit.

In one example, the NPCs are administered by injecting the NPCs with a syringe, inserting NPCs with a catheter or surgically implanting the NPCs. In certain embodiments, the NPCs are injected with a syringe into a body cavity that is fluidly-connected to the area of neurological or corporal deficit. In specific embodiments, the body cavity is a brain ventricle. In other embodiments, the NPCs are inserted with a catheter into a body cavity that is fluidly-connected to the area of neurological or corporal deficit. In still further additional embodiments, the NPCs are surgically implanted into a body cavity that is fluidly-connected to the area of neurological or corporal deficit. The NPCs can also alternatively be inserted using a syringe or catheter or surgically implanted directly at the site of the neurological or corporal deficit or systemically (e.g., intravenously).

EXAMPLES

Materials and Methods

Exosome Production and Isolation

For exosome production and isolation, first cells are grown on suspension or adhesion culture in high confluence. Then media containing exosomes is collected on 15 mL falcon tubes. This media is centrifuged at 4 celcius at 1200 rpm to remove debris. Then it is mixed 5 ml of polietilenglicol 20% in PBS and 200 uL of NaCl 7.4M for each 10 mL of supernatant from confluent cultures of NSC and iPS cells (this is done on 50 mL falcon tube. After 1-5 days of incubation at 4 Celsius, exosomes are precipitated by centrifugation at 10 000 rpm for 1 hour. Pellet containing exosomes is resuspended on PBS for experiments.

Identification of MSCs

Figure 6:
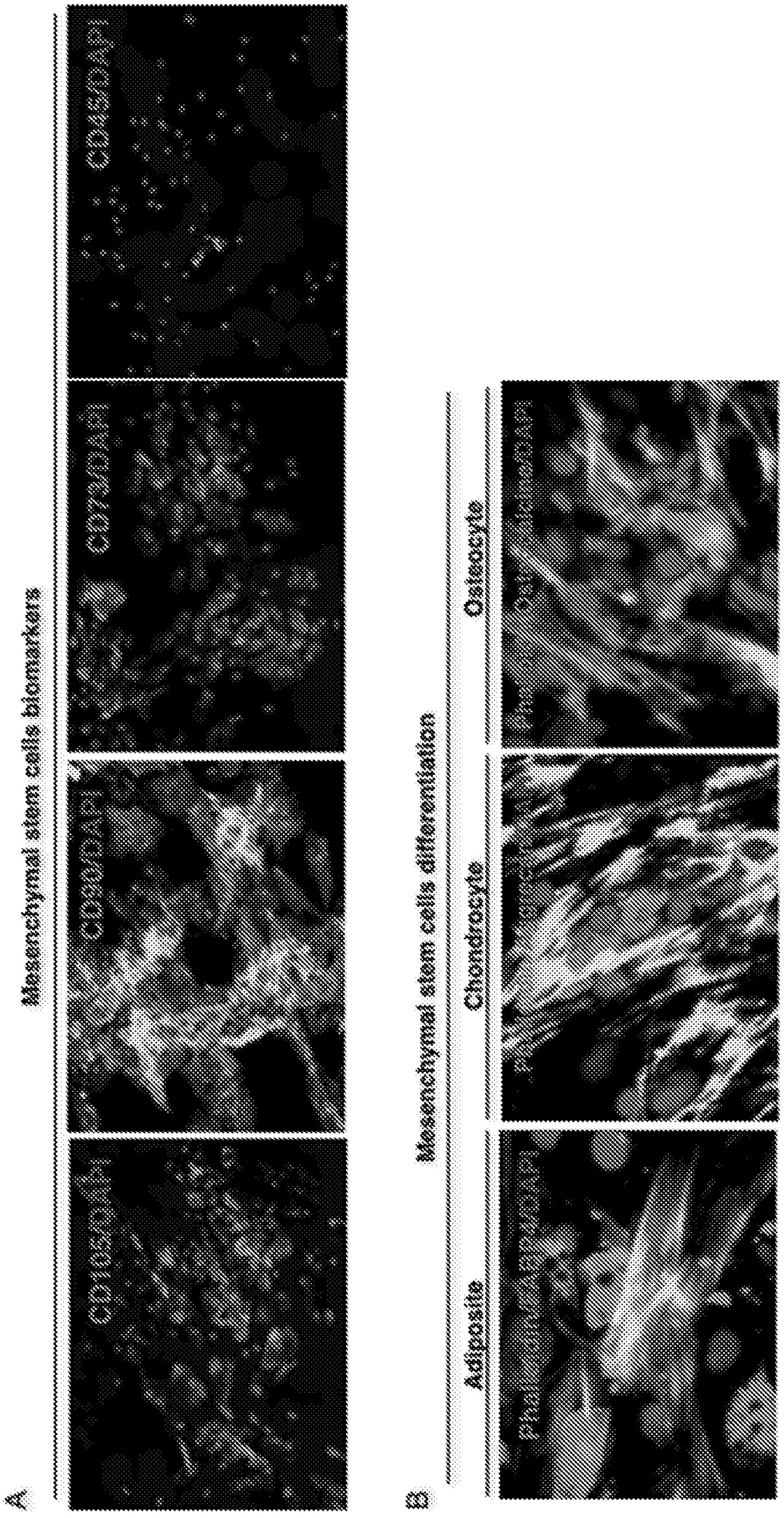
FIG. 6A provides micrographs showing presence of various mesenchymal stem cell markers.
FIG. 6B provides micrographs showing presence of various specific cell markers for cell types.

MSC are identified by their fibroblastic morphology on adherent cultures with a prominent nuclei under phase contrast microscope. In addition, we used fluorescence microscopy to identify positive markers: CD105, CD90, CD73 and negative marker CD45. In addition, we induce them to differentiate into osteocytes, adipocytes and chondrocytes and detect their markers osteocalcin, FABP4 and aggrecan respectively by fluorescent microscopy. FIG. 6 shows characterization by fluorescence microscopy.

MSC Media

MSC media contains DMEM F:12, 10% KSR, 5% Glutamax, 5% NNEA, 1% Penicillin/streptomycin. We used 12 well treated plates for production.

Isolation of Exosomes

To obtain NSC exosomes, NSC are grown in suspension in high densities on hNSC medium containing DMEM:F12, B27 supplement, rhFGF 10 ug/mL, rhEGF 20 ug/mL, Heparin 1000 U/mL, 1% antibiotic using non-adherent T75 flask. The cells are separated from media by gravity and supernatant containing extracellular vesicles is collected on 15 mL falcon tubes.

Similarly, to obtain iPS cell exosomes, IPS cells are grown using mTeSR media on 6 well plates coated with Vitronectin. The media is collected directly from cell cultures in 15 mL falcon tubes.

Example 1

FIG. 1 shows a diagram of the reprogramming steps of MSCs. MSCs are seeded in culture media and allowed to grow up under serum-free conditions until 80% confluence on adherent conditions using laminin as coat. In two methodologies, the epigenetic memory is considered, so that, in order to facilitate reprograming methylation marks on MSC gene commitment promoters are erased using decitabine (a drug also known as 5'-2-deoxycitidine which also inhibits DNMT3a activity), whose chemical structure is provided below.

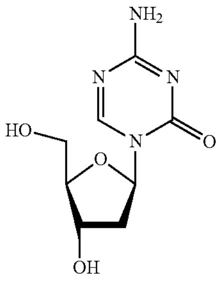

At stage 1, fresh media and NSC exosomes (and in two methodologies also we used pluripotent cells to enhance de-differentiation) as a source of linage specific signals, are provided to the cultured MSCs (typically following decitabine treatment), and exposed to NSC exosomes for 1-5 days. Following stage 1, (typically at day 5) stage 2 involves switching out media and NSC exosomes and exposing the cells to the fresh media and NSC exosomes for 5-15 days. After stage 2, (typically at day 15 from the start of stage 1) stage 3 involves switching out media and NSC exosomes with fresh media lacking NSC exosomes and allowing the cells to grow for 5-7 days. After stage 3, (typically at day 20-22 from the start of stage 1), neural progenitor spheres (the primary colonies) are isolated from the culture. After isolation occurs, the neurospheres are picked to keep on suspension for expansion and experimentation. Thus, the experiments results on conversion process for four methodologies which had the following conditions (all with NSC exosomes as common factor): Method 1: only NSC exosomes, Method 2: decitabine plus NSC exosomes, Method 3: only NSC and PS cells exosomes, and Method 4: decitabine plus NSC and PS cells exosomes. In an alternate embodiment, 5-Azacytidine may be used in combination or in place of decitabine to increase epigenetic status.

Example 2

Figure 2:
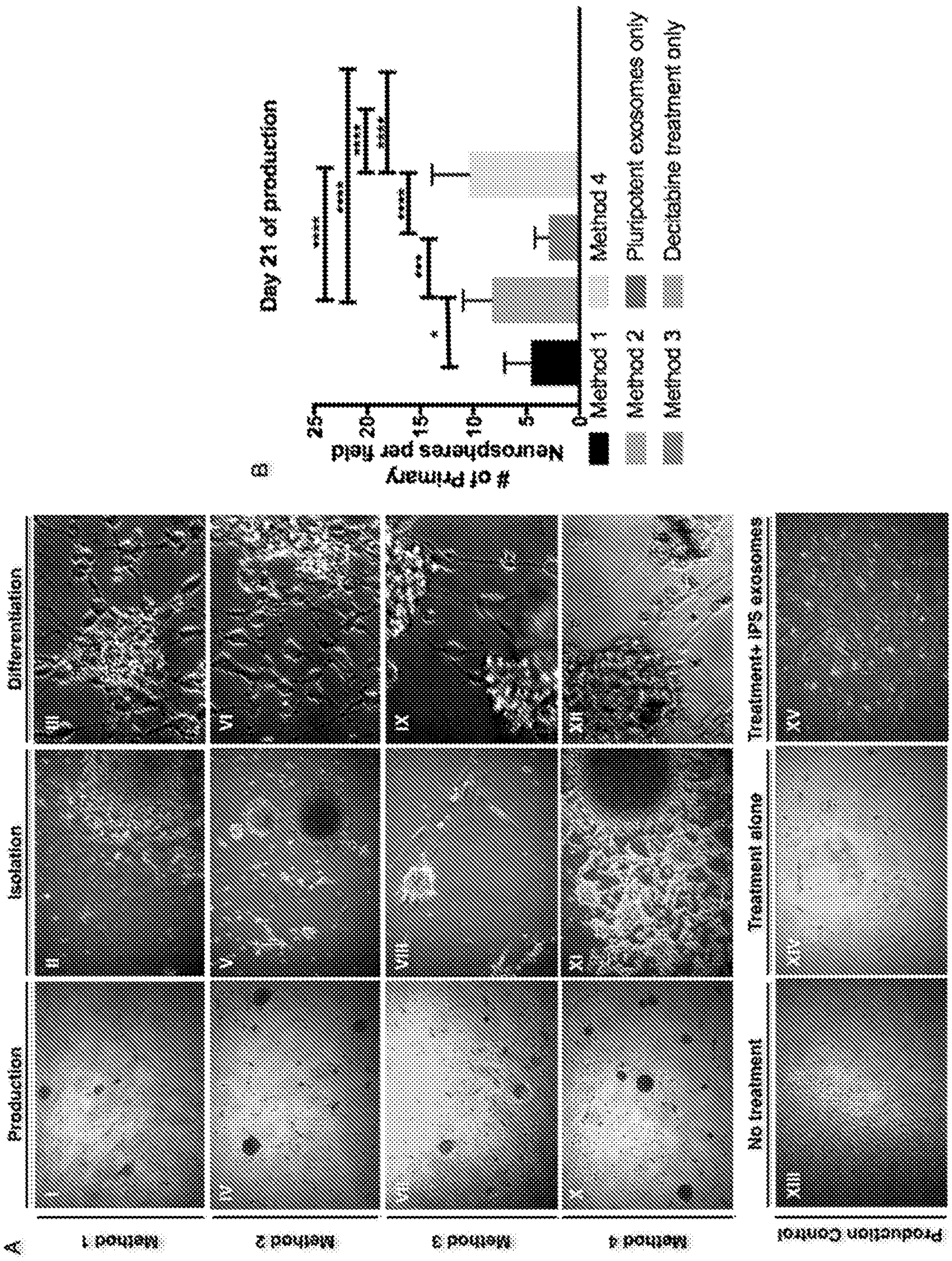
FIG. 2A shows micrographs of cells according to various method embodiments.
FIG. 2B shows a bar graph indicating production of neurospheres based on method embodiments.

FIG. 2 shows the general differences of production, isolation and differentiation between the four methodologies using NSC exosomes. As shown in FIGS. 2A and 2B, by day 21 of production, our methods changed morphologies of fibroblast-like shape typically found on MSC to a neural spherical clusters-like shape in all the methodologies. We found NSC-like clusters as early as day 15. However, different methodologies differ on the number of primary neurospheres produced, being method 4 the one that produces more spheres. It is of note that treatment with decitabine enhances the number of spheres produced (Methods 2 and 4). In addition, no spheres were found produced on cells without treatment, treatment (decitabine) or treated with decitabine and iPS exosomes.

Example 3

Figure 3:
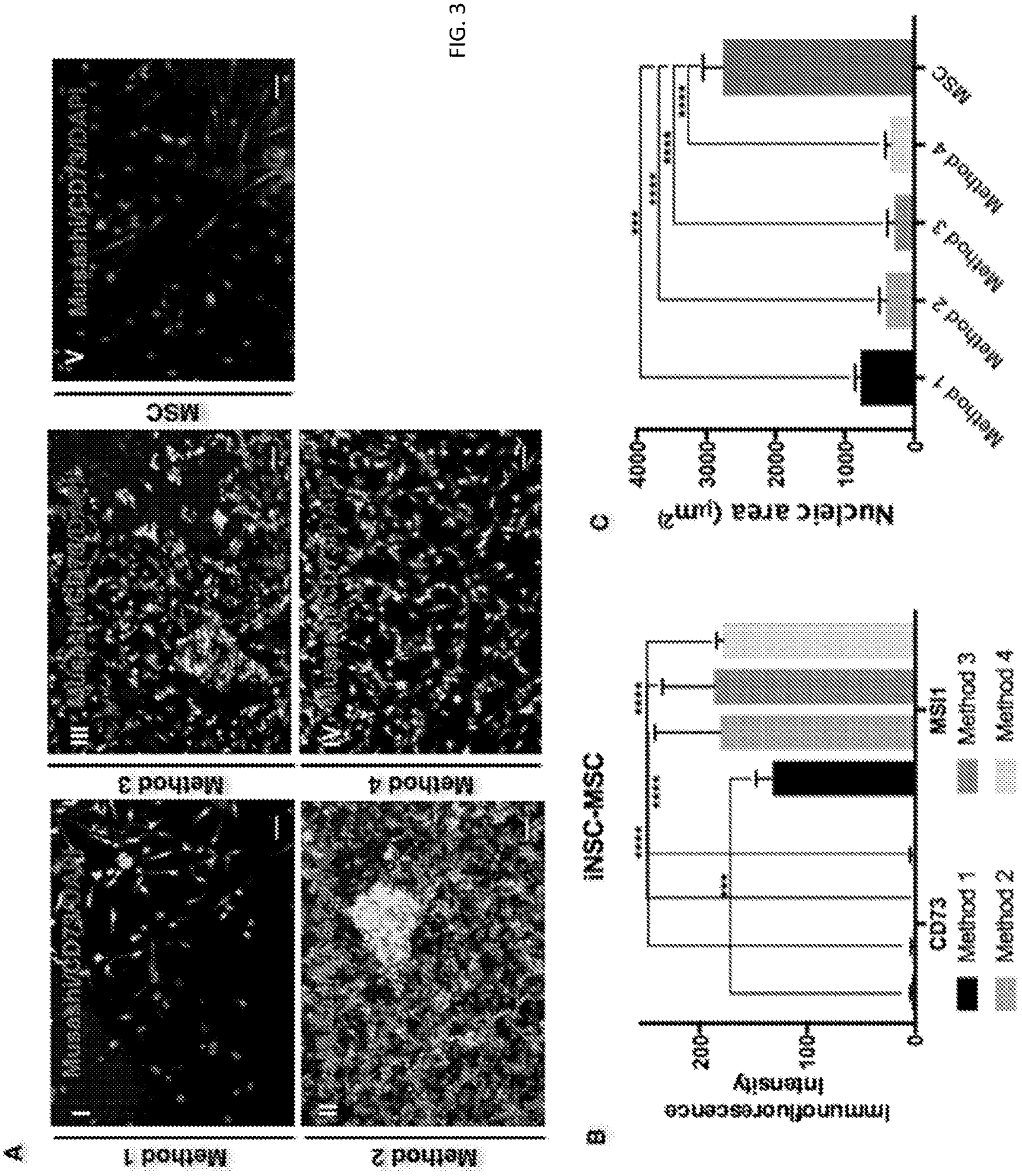
FIG. 3A shows micrographs of cells detecting various biomarkers in cell samples produced from different method embodiments.
FIG. 3B shows a bar graph demonstrating immunofluorescence of cells for certain markers.
FIG. 3C shows a bar graph showing the size of the nucleic area of cells treated by certain method embodiments.

FIG. 3 shows the characteristics of the resultant iNSC-MSC isolated. The primary colonies are positive staining for NSC marker Musashi1 (MSI1) in all the methods designed, whereas staining for MSC marker CD73 remains significantly not expressed (FIGS. 3A and 3B). Nevertheless, MSC indeed shows marker CD73 and lack of expression of MSI1. As shown in FIG. 3C, the nucleus area is significantly compacted in all the methodologies compared to the MSC nuclei area. And between the methods, the one using only NSC exosomes (Method 1) has the higher average of nuclei area compressed and lower MSI1 positive staining, since some cells resist to reprogram and keep the MSC like morphology (see FIG. 3A). All nuclei were counterstained with DAPI. Scale bar, 50 μm.

Example 4

Figure 4:
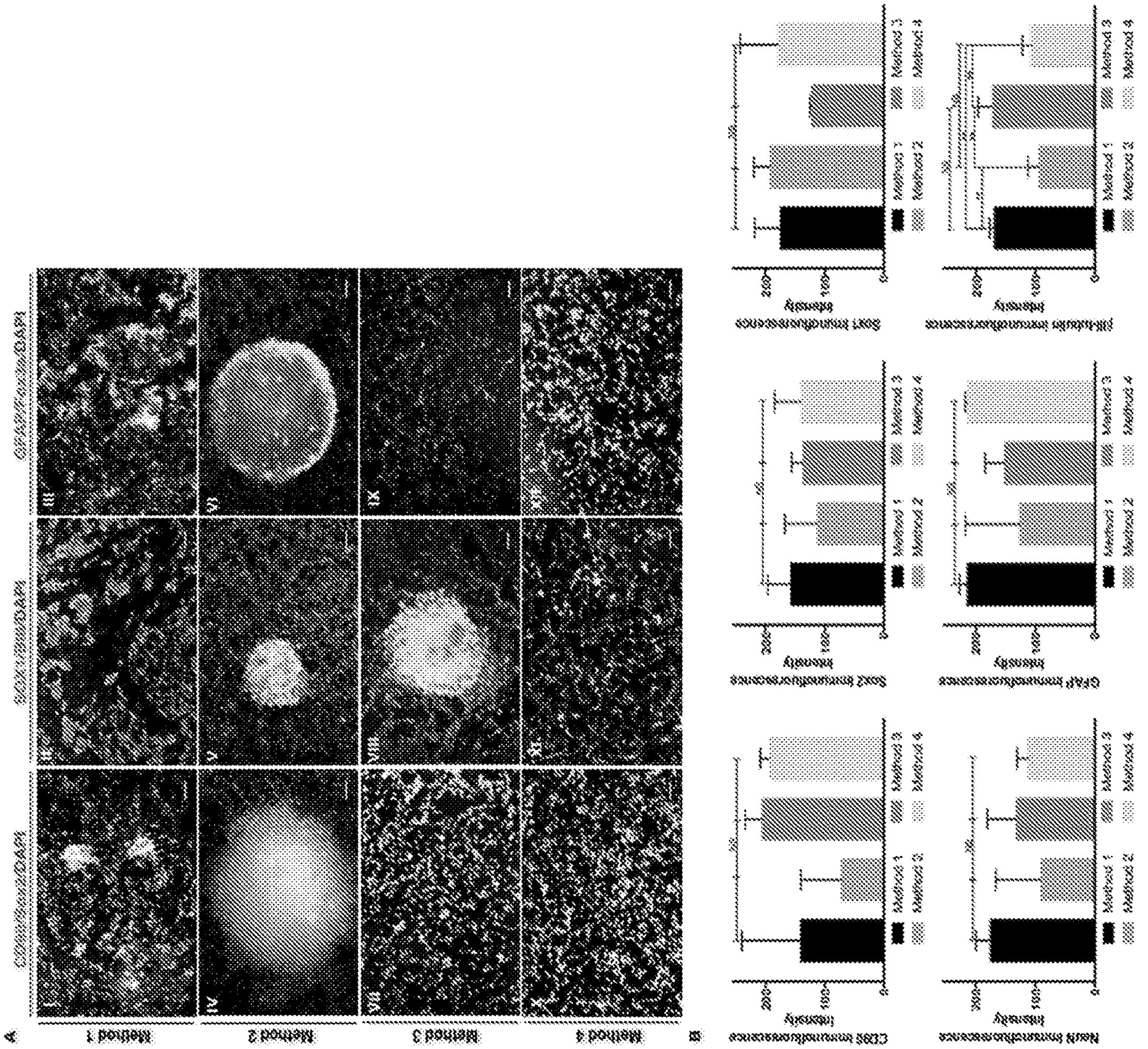
FIG. 4A shows micrographs of cells detecting various biomarkers in cell samples produced from different method embodiments.
FIG. 4B provides bar graphs demonstrating amount of the noted biomarkers observed in cells treated by certain method embodiments.

FIG. 4 shows the differentiation potential of iNSC-MSC under serum free conditions. The resultant cells of the four methods express neural differentiation markers BIII, GFAP and NeuN, especially in the surrounded areas of the spheres. On the other hand, they keep NSC markers Sox2, Sox1 and CD90 on the spheres. It is of noted that methods using decitabine (method 2 & 4) show significant less iimmunofluorescence intensities for BII tubulin, since this drug may decrease differentiation and retains stemness. All nuclei were counterstained with DAPI. Scale bar, 50 μm.

Example 5

Figure 5:
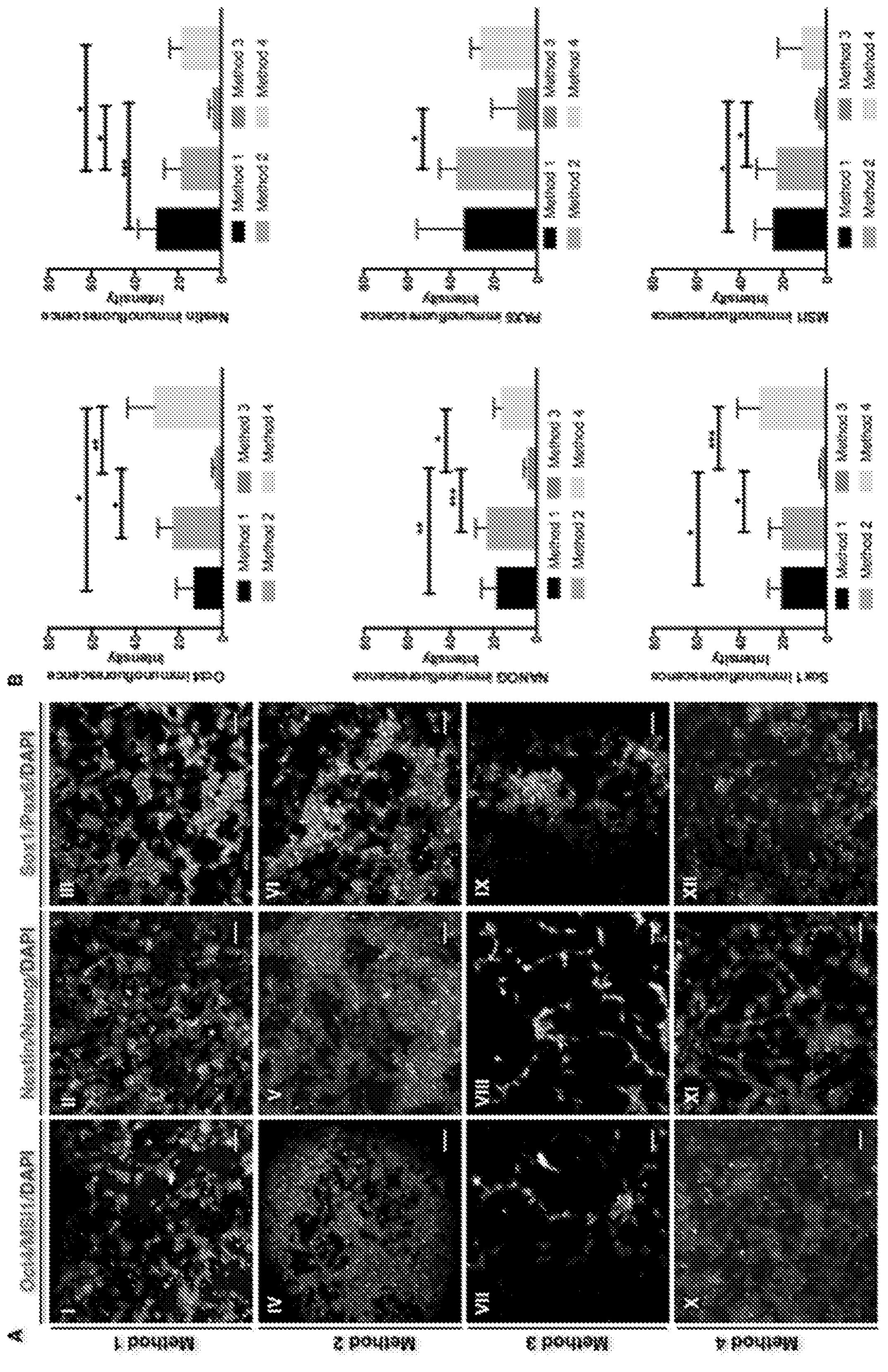
FIG. 5A shows micrographs of cells detecting various biomarkers in cell samples produced from different method embodiments.
FIG. 5B provides bar graphs demonstrating amount of the noted biomarkers observed in cells treated by certain method embodiments.

FIG. 5 shows characterization of expanded INSC-MSC. The resultant cells of the four methods express neural stem cell markers after isolated and expanded on suspension for several passages. iNSC-MSC are immunoreactive for neural stem cell markers MSI1, Sox1, Nestin, Pax6, and stemness markers Oct4 and nanog. It is of note that pluripotent exosomes may have an important role on the reprogramming and differentiation process and the quality of the NSC which is enhanced under decitabine which also facilitates the process. There is a significant difference between expression of neural stem cell markers of INSC-MSC produced with method 1 and method 3 (NSC exosomes, NSC exosomes and Pluripotent exosomes respectively) on MSI1, Sox1 and Nestin and at the stem cell marker nanog. There is a significant difference between INSC-MSC produced with method 3 and method 4 (NSC exosomes and Pluripotent exosomes, addition of decitabine with NSC exosomes and pluripotent exosomes respectively) at the specific stem cell marker sox1, and Nestin and at the stem cell markers Oct4 and nanog. All nuclei were counterstained with DAPI. Scale bar, 50 μm.

Example 6

FIG. 6 shows characterization of mesenchymal stem cells that have been reprogrammed. In FIG. 6A, suspended micrographs of MSCs are shown demonstrating that the cells present are positive for markers CD105, CD90 and CD73 and almost negative for marker CD45. The micrographs of FIG. 6B show that adherent cultures of MSC are immunoreactive for FABP4, aggrecan and osteocalcin when direct differentiation is done to develop adipocytes chondrocytes and osteocytes, and respectively. It is shown F-actin with phalloidin of cells and the nuclei counterstained with DAPI.

Embodiments illustrated herein by the experiments described above and by the examples, should not be construed as limiting. The contents of all references, pending patent applications and published patents, cited throughout this application are hereby expressly incorporated by reference. Those skilled in the art will understand that this invention may be embodied in many different forms and should not be construed as limited to the embodiments set forth herein. Rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

What is claimed is:

1. A method of reprogramming mesenchymal stem cells as neural progenitor cells, the method comprising (a) modifying epigenetic status of mesenchymal stem cells by (i) subjecting the mesenchymal stem cells to a first media comprising 5-aza-2'-deoxycytidine; (ii) removing the first media from the mesenchymal stem cells, and (iii) subjecting the mesenchymal stem cells from step (ii) to a second media comprising SB431542; and (b) contacting the mesenchymal stem cells of step (a) with extracellular vesicles obtained from neural stem cells under conditions to allow the mesenchymal stem cells to convert into neural progenitor cells.

2. The method of claim 1, wherein contacting step (b) comprises (iv) culturing the mesenchymal stem cells in media with neural stem cell (NSC) exosomes for 1-5 days; after step (iv), (v) refreshing the media and NSC exosomes and culturing the cells for 5-15 days; and after step (v), (vi) providing fresh media lacking NSC exosomes and culturing the cells for at least 5-7 days, wherein the cells of step (vi) form spheres.

3. The method of claim 2, further comprising isolating spheres from step (vi).

4. The method of claim 2, wherein step (v) starts at day 4, 5, or 6 from the start of step (iv); and step (vi) starts at day 14, 15, or 16 from the start of step (a).

5. The method of claim 1, wherein contacting step (b) results in formation of spheres, and the method further comprises (c) isolating the spheres.

6. The method of claim 1, wherein the extracellular vesicles comprise exosomes.

* * * * *